United States Patent [19]

Dols

[11] 3,937,735

[45] Feb. 10, 1976

[54] PROCESS FOR THE PREPARATION OF CYCLOHEXANONE

[75] Inventor: Peter L. M. Dols, Geleen, Netherlands

[73] Assignee: Stamicarbon B.V., Geleen, Netherlands

[22] Filed: Nov. 21, 1973

[21] Appl. No.: 418,021

[30] Foreign Application Priority Data

Nov. 23, 1972 Netherlands.................... 7215853

[52] U.S. Cl........ 260/586 P; 260/610 B; 260/631 R
[51] Int. Cl.² ................ C07C 27/04; C07C 27/12; C07C 45/16; C07C 45/02
[58] Field of Search ........ 260/586 R, 586 B, 631 R, 260/610 B, 586 P

[56] References Cited
UNITED STATES PATENTS

| | | | |
|---|---|---|---|
| 1,892,011 | 12/1932 | Sandkuhl........................ | 260/586 R |
| 1,895,516 | 1/1933 | Jazier.............................. | 260/586 R |
| 2,497,349 | 2/1950 | Farkas et al. ................... | 260/631 R |
| 3,355,282 | 11/1967 | Kudo et al. ..................... | 260/586 R |
| 3,694,511 | 9/1972 | Nouvel............................ | 260/586 R |

*Primary Examiner*—Norman Morgenstern
*Attorney, Agent, or Firm*—Cushman, Darby & Cushman

[57] ABSTRACT

A process is described for the preparation of cyclohexanone by oxidation of cyclohexane in the liquid phase with oxygen or a gas containing oxygen, under conditions so that the oxidation product contains cyclohexyl hydroperoxyde, followed by catalytically hydrogenating the said oxidation product with a hydrogen gas-containing stream in a hydrogenating zone, whereby the said cyclohexyl hydroperoxide is converted substantially to cyclohexanol, and catalytically dehydrogenating the said cyclohexanol together with cyclohexanol produced in the oxidation reaction to cyclohexanone and hydrogen, separating the said cyclohexanone and passing at least part of the resulting hydrogen containing gas stream to the said hydrogenating zone to effect the said hydrogenation of the oxidation product.

4 Claims, No Drawings

PROCESS FOR THE PREPARATION OF CYCLOHEXANONE

This invention relates to a process for the preparation of cyclohexanone in which cyclohexane is oxidized in the liquid phase with oxygen or with a gas containing oxygen. Such processes are known in the art and employed on an industrial scale. Cyclohexanone is an important intermediate in several chemical syntheses, i.a. in the synthesis of nylon-6-6 via adipic acid, and of nylon-6 via ε-caprolactam.

Oxidation of cyclohexane in the liquid phase with oxygen or an oxygen containing gas, invariably yields cyclohexanol as a byproduct together with the desired cyclohexanone. The practice of converting this cyclohexanol to cyclohexanone by catalytic dehydrogenation is well-known. The hydrogen gas formed in this operation is normally not suitable for use in chemical syntheses due to the organic impurities it contains. Even after being cooled to remove as much as possible of the impurities by condensation, the hydrogen gas can only be used as fuel gas of very low thermal value.

The invention provides a method for the preparation of cyclohexanone in which the byproduct comprising contaminated hydrogen gas can be usefully employed.

The invention provides a process for the preparation of cyclohexanone by the oxidation of cyclohexane in the liquid phase with oxygen or an oxygen-containing gas, comprising effecting the said oxidation under conditions so that the oxidation product contains cyclohexyl hydroperoxide, catalytically hydrogenating the said oxidation product in a hydrogenation zone with a hydrogen gas-containing stream, obtained as hereinafter set forth, whereby the said cyclohexyl hydroperoxide is converted substantially to cyclohexanol, and catalytically dehydrogenating the said cyclohexanol, together with cyclohexanol produced in the oxidation reaction, to cyclohexanone and hydrogen, separating the said cyclohexanone and passing at least part of the resulting hydrogen gas-containing stream to the said hydrogenating zone to effect the said hydrogenation of the oxidation product.

The impurities in the hydrogen obtained from the dehydrogenation do not effect the hydrogenation of the oxidation product. A particular advantage of the process according to the invention is that the amount of hydrogen formed in the dehydrogenation reaction is sufficiently large for hydrogenating all products that have to be hydrogenated, which renders the process independent of the availability of a hydrogen plant. In fact a hydrogen plant cannot be operated on a profitable basis merely to supply no more than the relatively small volume of hydrogen needed for this hydrogenation in a cyclohexane oxidation unit of normal size. However, if a hydrogen plant is available with an economically justified capacity, it would be necessary to find outlets for the large volume of hydrogen becoming available from it. Such a requirement however is not required by the practice of the present invention.

The volume of hydrogen set free in the dehydrogenation step in the process of the invention is however considerably larger than the volume required in the hydrogenation step. Moreover the said hydrogen is free of inert constituents, with the consequence that the partial hydrogen pressure on the exit side of the hydrogenation zone is substantially equal to that on inlet side. As a consequence the recirculation of a portion of the gases leaving the hydrogenation zone to the entrance side of said zone, as is normal practice in hydrogenation processes, can now be omitted, it being sufficient to discharge the unconverted hydrogen, if desired after removal of organic constituents. This eliminates the need of a recirculation compressor, and the products to be hydrogenated can be converted to a sufficiently high degree.

Preferably the oxidation is effected under conditions so that at least 25 % weight of the oxygen containing constituents of the oxidation product consists of cyclohexyl hydroperoxide.

Such a cyclohexane oxidation product can be obtained for example by allowing the oxidation to take place in a reactor having a wall which is inert to the reaction, i.e. that has no substantial catalytic effect on the decomposition of the peroxides, and which does not provide a reagent to the reaction mixture, e.g. transition metal ions, which tends to promote such a decomposition. Such a wall may consist e.g. of aluminium, tantalum, glass or, preferably phosphated steel. Under certain conditions it may be advantageous however not to exclude the presence of any transition metal ions in the reaction mixture, and possibly it may be advantageous to add such ions deliberately, the oxidation reaction then proceeding at a faster rate, while the metal ion concentration will be sufficiently low to achieve and maintain the desired content of peroxides in the reaction mixture. Additives suitable for such purposes are cobalt naphthenate and chromium octoate.

The oxidation reaction is preferably carried out at a temperature of from 120°–190°C. The reaction pressure is not critical, provided that it is sufficiently high to maintain a liquid phase in the system. The preferred degree of conversion based on the amount of cyclohexane supplied, is between 1 % and 12 %. Air, or air diluted with a portion of the off gas, can be employed as the oxygen-containing gas.

It is preferred to hydrogenate the peroxide in the presence of a catalyst system containing palladium, or other catalysts, e.g. platinum, nickel or rhodium can be used. The catalyst is preferably deposited on a carrier, e.g. aluminium oxide, carbon or silica. The hydrogenation can be carried out at the same temperature and the same pressure as the oxidation reaction, but lower or higher temperatures and pressures can be employed if desired. The temperature is preferably chosen below 120°C and above 30°C.

The hydrogenation catalyst may be present in a fixed bed. To achieve a reasonably fast conversion rate, it will be necessary then to use a temperature of at least 80°C and a partial hydrogen pressure of at least 10 atm. Lower temperatures and pressures are also possible but require a longer residence time, and thus a larger reaction vessel to achieve a given rate.

The hydrogenation catalyst may be suspended in the liquid reaction mixture, the hydrogenation reaction then proceeding at a satisfactory rate at room temperature and 1 atmosphere pressure. Under these conditions, the yields of cyclohexanol and cyclohexanone will be higher than when the hydrogenation is carried out with a catalyst on fixed bed.

The following Examples of the invention are provided.

EXAMPLE I

In a continuous process comprising oxidation in a pressure vessel having an inner lining of aluminium containing no metal compounds of liquid cyclohexane at 160°C and 10 atmospheres pressure with air as the oxidizing agent, subsequently a part of the unconverted cyclohexane was removed by distillation at 90°C and reduced pressure, and 144.6 kg/hour of a mixture was produced which, in addition to cyclohexane, contained 20.2 % wt of cyclohexyl hydroperoxide, 10.3 % wt of cyclohexanol, 6.9 % wt of cyclohexanone and 6.4 % wt of byproducts. The yield of cyclohexyl hydroperoxide, cyclohexanol, and cyclohexanone totalled 84.5 % based on cyclohexane converted.

The said mixture was introduced into a hydrogenation zone wherein it was contacted countercurrently with a stream of a hydrogen-containing gas (9.1 nm$^3$/h) at 15 atmospheres pressure obtained as hereinafter described, using a supported palladium catalyst in a fixed bed having a palladium content of 0.1 % wt based on aluminium oxide support. The temperature in the hydrogenation zone was maintained at 110°C, and the residence time of the liquid therein was 15 minutes. The excess of hydrogen (3.4 nm$^3$/h) leaving the hydrogenation zone on the exit side was cooled to 10°C to condense the bulk of the organic constituents, and was subsequently removed from the system. The condensate was recycled to the oxidation stage.

The resulting mixture substantially comprising cyclohexanol and cyclohexanone in a 4.0/1 ratio, and cyclohexane, was then introduced to a distillation column (hereinafter referred to as 'cyclohexane column') wherein the cyclohexane was distilled off. The water contained in the mixture was discharged as a component of the cyclohexane-water azeotrope. Upon condensation and removal of the water, the cyclohexane thus recovered was recycled to the oxidation stage, and the residual mixture subsequently separated into a fraction of low-boiling byproducts (mainly alcohols), a cyclohexanone fraction, a cyclohexanol fraction and a fraction of high-boiling byproducts. Without requiring further purification, the cyclohexanone fraction thus obtained may be further processed e.g. to cyclohexanone oxime, which can be converted to ε-caprolactam.

The cyclohexanol fraction was passed in vapour form over a zinc-iron catalyst at 390°C, 1.1 atmospheres pressure and 0.4 sec residence time, to provide 9.1 nm$^3$/hour of hydrogen containing gas, which upon condensation of the organic constituents and cooling to 90°C, still contained some cyclohexanol and cyclohexanone. This hydrogen gas-containing stream was compressed and supplied to the hydrogenation zone. The organic condensate consisted substantially of cyclohexanone and cyclohexanol in a molar ratio of approximately 1.5/1, and was combined with the organic mixture flowing down from the cyclohexane column after having been freed of cyclohexane and water.

Calculated to the total amount of cyclohexane converted the yield of pure cyclohexanone from the overall process was 83 %, based on the total cyclohexane converted.

The heat content of the exit gases issuing from the dehydrogenation zone, and consisting mainly of cyclohexanone, cyclohexanol and hydrogen, can be utilized for supplementing the amount of heat withdrawn from the contents of the cyclohexane column by the evaporation of cyclohexane and water. The heat of condensation of the cyclohexanone and cyclohexanol will thus be retained in the system.

EXAMPLE II

Cyclohexane was oxidized in a manner similar to that described in Example I, the removal by distillation of the cyclohexane after the oxidation being effected however by decompressing the reaction mixture to 1 atm pressure without additional supply of heat.

The concentrated mixture was introduced to a hydrogenation zone in which 1 g of catalyst, comprising 10 parts by weight of palladium on a carbon carrier, was maintained in suspension per liter of suspending liquid. The particle size of the catalyst, defined as $\bar{d}_{rs}$ as determined by the CO-absorption method of Scholten and van Montfoort, J. of Catalysis 1 (1962), 85–92, was in the range 20–200 A. The stirring rate was 2000 rpm. Catalyst particles depositing on the walls of the hydrogenation reactor were continuously washed down by the inflowing reaction mixture. The residence time of the liquid in the hydrogenation zone was 20 minutes. 9.2 nm$^3$/h of hydrogen, containing gas obtained as hereinafter described, were supplied. The temperature in the zone was maintained at 30°C, the pressure being 1 atmosphere.

Upon removal of the catalyst from the suspension by continuous filtration, the reaction mixture substantially consisted of cyclohexanol and cyclohexanone in a molar ratio of 2.3/1, and cyclohexane. The cyclohexane was removed from the mixture in the manner described in Example I, whereupon the mixture was separated into a cyclohexanone fraction, a light byproduct fraction, a heavy byproduct fraction and a cyclohexanol fraction. By means of the procedure set forth in Example I, the cyclohexanol fraction was dehydrogenated to yield a mixture of cyclohexanone and cyclohexanol in a molar ratio of 1.5/1, which was then recycled to the distillative separation zone. The hydrogen gas saturated with cyclohexanol and cyclohexanone set free in the dehydrogenation reaction was introduced into the hydrogenation zone.

The yield, based on converted cyclohexane, was to 84 %.

Compared with the process of Example I, the process of Example 2 offers the advantage that after the product mixture from the oxidation stage has been expanded, the entire process proceeds at one and the same pressure.

The process can be modified by performing the hydrogenation at the boiling temperature of the reaction mixture. The reaction water and the heat of reaction can then be easily removed by evaporation of cyclohexane and water. The evolving vapours can be condensed, and the organic layer formed upon separation into layers by recycled to the oxidation or hydrogenation stage.

I claim:

1. A process for the preparation of cyclohexanone which comprises oxidizing cyclohexane in the liquid phase with oxygen or an oxygen-containing gas, to produce an oxidation reaction product containing cyclohexyl hydroperoxide, catalytically hydrogenating the said oxidation product in a hydrogenation zone in the presence of a catalyst containing palladium, platinum, nickel or rhodium with a hydrogen gas-containing stream, obtained as hereinafter set forth, whereby the said cyclohexyl hydroperoxide is converted substantially to cyclohexanol, recovering the cyclohexanol fraction by distillation and catalytically dehydrogenating the said cyclohexanol, to cyclohexanone and hydrogen, separating the said cyclohexanone and passing the resulting hydrogen gas-containing stream to the said hydrogenating zone to effect the said hydrogenation of the oxidation product.

2. A process according to claim 1, wherein the oxidation is effected under conditions so that at least 25 % weight of the oxygen containing constituents of the oxidation product consists of cyclohexyl hydroperoxide.

3. A process according to claim 1 wherein the catalytic hydrogenation is effected in the presence of a suspended palladium catalyst.

4. A process according to claim 1, wherein said oxidation is effected at a temperature of from about 120°–190°C and said hydrogenating is effected at a temperature of from about 30°–120°C.

* * * * *